United States Patent [19]

Pfirmann et al.

[11] Patent Number: 5,446,198
[45] Date of Patent: Aug. 29, 1995

[54] 4-HYDROXY-2,3,5-TRIFLUOROBENZOIC ACID AND A PROCESS FOR ITS PREPARATION

[75] Inventors: Ralf Pfirmann, Griesheim; Rainer Wingen, Hattersheim am Main, both of Germany

[73] Assignee: Hoechst Aktiengesellschaft, Frankfurt am Main, Germany

[21] Appl. No.: 167,428

[22] Filed: Dec. 15, 1993

[30] Foreign Application Priority Data

Dec. 17, 1992 [DE] Germany ............... 42 42 696.0

[51] Int. Cl.⁶ ............................................. C07C 59/00
[52] U.S. Cl. .................................................. 562/465
[58] Field of Search ........................................ 562/465

[56] References Cited

U.S. PATENT DOCUMENTS

| | | | |
|---|---|---|---|
| 3,413,341 | 11/1968 | Bursack et al. | 260/521 |
| 3,459,794 | 8/1969 | Tamborski | 260/516 |
| 5,227,535 | 7/1993 | Pfirmann et al. | 568/709 |
| 5,292,967 | 3/1994 | Papenfuhs et al. | 568/709 |

FOREIGN PATENT DOCUMENTS 60-204742 10/1985 Japan .
2225438 9/1990 Japan .

OTHER PUBLICATIONS

Patent Abstract of Japan, vol. 10, No. 67 (C–333) (2124) Mar. 15, 1986.

*Primary Examiner*—Paul J. Killos
*Attorney, Agent, or Firm*—Connolly & Hutz

[57] ABSTRACT

The present invention relates to the novel compound 4-hydroxy-2,3,5-trifluorobenzoic acid and to a process for preparing this novel substance by reacting 2,3,4,5-tetrafluorobenzoic acid at elevated temperature with a basic compound dissolved and/or suspended in water, adding, if desired, a fluoride scavenger, bringing the resulting reaction mixture to a pH of 0 to 6 by addition of an acid, and isolating the 4-hydroxy-2,3,5-trifluorobenzoic acid formed.

1 Claim, No Drawings

4-HYDROXY-2,3,5-TRIFLUOROBENZOIC ACID AND A PROCESS FOR ITS PREPARATION

The present invention relates to the novel compound 4-hydroxy-2,3,5-trifluorobenzoic acid and to a process for its preparation. The novel substance can be used for preparing novel liquid-crystalline compounds having advantageous properties. The synthesis of these liquid-crystalline compounds and their use in displays and their novel advantageous properties form the subject-matter of a separate application (Reference P 4242695.2) entitled "Trifluorophenyl compounds, a process for their preparation and their use in liquid-crystalline mixtures". That application has the same priority date as the present invention. Scheme 5 enclosed with that application shows the synthetic route leading to the liquid-crystalline compounds in simplified form. The corresponding scheme is reproduced in the present application without any additional explanations, solely for the purpose of illustration (see reaction scheme).

To prepare 4-hydroxy-2,3,5-trifluorobenzoic acid, 2,3,4,5-tetrafluorobenzoic acid is advantageously used as the starting material. This starting material can be prepared by methods known from the literature (DE 3,810,093; EP 0,218,111; EP 0,194,671). 2,3,4,5-Tetrafluorobenzoic acid is reacted with a basic compound present as a solution and/or suspension in water at elevated temperature. If desired, a fluoride scavenger is added, the resulting reaction mixture is brought to a predetermined pH by addition of an acid, and the 4-hydroxy-2,3,5-trifluorobenzoic acid formed is isolated.

The reaction proceeds in accordance with the following formula scheme:

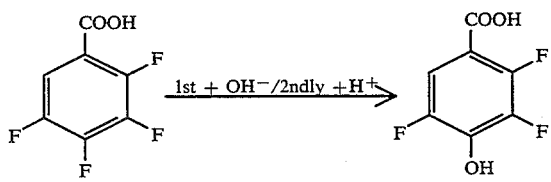

in which the fluorine atom in the 4 position is exchanged for a hydroxyl group.

Usually, the basic compound is dissolved in water, and this aqueous solution is used directly in the reaction. However, in those cases in which the basic compound does not dissolve in water to the desired extent, it is also possible to use a suspension of the basic compound in water. Advantageously, the basic compound is used in a concentration of 3 to 50, in particular 5 to 40, preferably 10 to 25, % by weight, based in each case on the aqueous solution or the aqueous suspension.

Suitable basic compounds are basic compounds of alkali metals and/or alkaline earth metals. These include alkali metal oxides, alkali metal hydroxides, basic alkali metal salts, alkaline earth metal oxides, alkaline earth metal hydroxides and/or basic alkaline earth metal salts. Suitable basic compounds are lithium hydroxide, sodium hydroxide, potassium hydroxide, rubidium hydroxide, cesium hydroxide, lithium bicarbonate, lithium carbonate, sodium bicarbonate, sodium carbonate, potassium bicarbonate, potassium carbonate, basic sodium phosphate, basic potassium phosphate, magnesium hydroxide, calcium hydroxide, strontium hydroxide and/or barium hydroxide.

Highly suitable basic compounds are sodium hydroxide, potassium hydroxide and/or calcium hydroxide, in particular sodium hydroxide and/or potassium hydroxide, preferably sodium hydroxide. Using mixed salts, for example basic carbonates and phosphates or else mixtures of these basic compounds, also gives good results.

When carrying out the reaction according to the invention, care must be taken that the basic compound is used in a sufficient amount for effecting the desired substitution of the fluorine atom in the 4 position. Usually, the basic compound is used in such an amount that 3 to 10, in particular 3.1 to 4.8, preferably 3.3 to 4.2 mol, of hydroxide ions are available per mole of 2,3,4,5-tetrafluorobenzoic acid.

Although the reaction of 2,3,4,5-tetrafluorobenzoic acid proceeds even at comparatively low temperatures, it is advisable to carry out the reaction at elevated temperature. Carrying out the reaction at 50° to 180° C. usually gives good results. In most cases, it is sufficient to carry out the reaction at a temperature of 70 to 130, in particular 90° to 110, ° C. The reaction temperature to be selected depends, inter alia, not only on the amounts of the substances to be used but also on the nature and concentration of the basic compound. Moreover, the size of the reaction batch and the type of reactor used also play a part to a limited extent. Higher reaction temperatures, in particular those above 100° C., usually make it necessary to carry out the reaction under superatmospheric pressure. This means that the reactor used must be designed for such a mode of operation. In contrast, temperatures below 100° C. usually make it possible to carry out the reaction under atmospheric pressure.

A particular advantage of the process according to the invention is that the reaction can be carried out in the absence of an additional solvent, in particular an organic solvent. In view of the fact that organic solvents act as solubilizers, it is surprising that such a solvent need not be added in the reaction and yet the desired compound is obtained in high yield and high purity. Surprisingly, byproducts, in particular the isomeric 3-hydroxy-2,4,5-trifluorobenzoic acid, are only formed to a comparatively small extent. This byproduct is usually present in an amount of less than 6 mol %. Apart from the high selectivity, it is particularly surprising that the reaction proceeds at the temperatures according to the invention, since the carboxylate grouping has, if anything, a deactivating effect on this type of reaction. For the same reason, the hydroxyl group would be expected to enter the 3 or 5 position since in this case no interference from the interaction of two negative charges would be expected in the transition state. Accordingly, it is particularly surprising that of 4 possible fluorine atoms only one is exchanged with high selectivity and the exchange of a second fluorine atom also takes place only to a minor degree.

During workup of the reaction mixture formed, there is a risk of the reactors used being damaged by corrosion caused by hydrogen fluoride formation. This corrosion can be minimized and suppressed to a suprisingly large extent by addition of fluoride scavengers. Suitable fluoride scavengers are calcium salts and/or silicon compounds. Calcium salts which can be used are calcium chloride, calcium sulfate and/or calcium hydroxide and silicon compounds which can be used are various silicates, silica gels and/or silicon dioxide, in particular silicon dioxide having increased inner surface area. The fluoride scavengers are usually used in a 0.5- to 10-fold, in particular 1.5- to 4-fold, amount, relative to the theoretically formed amount of fluoride. It is surprising that the corrosion caused by hydrofluoric acid can also be largely suppressed in the dilute aqueous solution formed in the process according to the invention.

The reaction gives the 4-hydroxy-2,3,5-trifluorobenzoic acid not in the form of the free acid but as an aqueous solution of a salt. In order to liberate the free 4-hydroxy-2,3,5-trifluorobenzoic acid from the aqueous solution of its salts, the reaction mixture is acidified. The acid used can be a mineral acid, in particular a non-oxidizing mineral acid, or an organic acid of sufficient acid strength. Suitable mineral acids are sulfuric acid, phosphoric acid, hydrochloric acid, hydrobromic acid and/or hydriodic acid and suitable organic acids are formic acid, halogenated or non-halogenated acetic acid, aromatic and/or aliphatic sulfonic acids or mixtures of these acids.

The amount of acid added is usually such that a pH of 0 to 6 is reached. In many cases, it has proven favorable to adjust the pH to a value of 0.1 to 4, in particular 1 to 3.

The 4-hydroxy-2,3,5-trifluorobenzoic acid liberated by acidification is isolated from the reaction mixture formed by extracting the reaction mixture with a suitable solvent. Suitable solvents for this purpose are ethers, in particular aliphatic ethers, for example MTBE (methyl tert.-butyl ether), di-n-butyl ether, and/or esters, in particular esters of aliphatic carboxylic acids, preferably alkyl acetate or alkoxyalkyl acetate, for example methyl acetate, ethyl acetate, butyl acetate or 3-methoxybutyl acetate. The solvent is distilled off, and the valuable product obtained is recrystallized from a suitable solvent, for example 1,2-dichlorobenzene, chlorobenzene, toluene, xylene, chlorotoluene, cyclohexane, methylcyclohexane. Another way is to remove the water from the reaction mixture formed after acidification by azeotropic distillation using an organic solvent, for example cyclohexane, toluene, xylene, chlorobenzene or 1,2-dichlorobenzene, to filter the hot suspension, which removes any salts present, and to crystallize the valuable product by cooling the aqueous solution. Further purification is carried out as mentioned above by recrystallization from a solvent suitable for this.

The example which follows illustrates the invention without limiting it.

EXAMPLE 50 g (0.258 mol) of 2,3,4,5-tetrafluorobenzoic acid and 41.4 g (1.04 mol) of sodium hydroxide are introduced first into 687 g of water, the resulting solution is heated to 100° C. and stirred at this temperature for 12 to 14.5 hours. The end point of the reaction is determined by gas chromatography. 57.2 g of calcium chloride are then added, and the pH is brought to 1 with 30% hydrochloric acid. The solution is continuously extracted with MTBE (methyl tert.-butyl ether) for 16 hours, and the solvent is then distilled off. The dry residue (44.6 g) is recrystallized at 145° C. from 1,2-dichlorobenzene to give 42.1 g (0.219 mol, 85%) of white to slightly beige-colored 4-hydroxy-2,3,5-trifluorobenzoic acid which gives the expected values in all analytical tests. The 3-hydroxy-2,4,5-trifluorobenzoic acid content of less than 5 mol % of the crude product also formed in the reaction is completely removed by dissolution and reprecipitation (recrystallization).

Alternatively, the product can be isolated by removal of the water from the mother liquor by azeotropic distillation using xylene or 1,2-dichlorobenzene, filtering off the suspension obtained while hot from the undissolved salts, and then allowing the product to crystallize. The required further purification is carried out as described above by repeated crystallization from 1,2-dichlorobenzene or xylene.

Using potassium hydroxide (56.1 g, 1 mol) instead of sodium hydroxide and acidifying with hydrochloric acid and using calcium hydroxide (30 g) instead of calcium chloride as the fluoride scavenger give essentially the same result.

It is possible to use lithium carbonate (88.7 g), lithium hydroxide hydrate (37.8 g) or calcium hydroxide (148.2 g) instead of sodium hydroxide, giving the same result. If sulfuric acid or phosphoric acid is used instead of hydrochloric acid for acidifying the reaction mixture, essentially the same result is obtained.

M.p. (DSC): 164.1° C.

$^1$H NMR [DMSO-d$_6$/ppm]: $\delta = 7.46$ (q, 1H, $J_{AD}=11.3$ Hz, $J_{BD}=6.6$ Hz, $J_{CD}=2.4$ Hz, Ar-H$^6$ (D))

$^{19}$F NMR [DMSO-d$_6$/ppm]: $\delta = -136.26$ (q, 1 F, $J_{AD}=11.3$ Hz, $J_{AB}=12.7$ Hz, $J_{AC}=9.4$ Hz, Ar-F$^5$ (A)) $-138.6$ (q, 1 F, $J_{BD}=6.6$ Hz, $J_{AB}=12.7$ Hz, $J_{BC}=21.0$ Hz, Ar-F$^2$ (B)) $-154.94$ (q, 1F, $J_{CD}=2.4$ Hz, $J_{BC}=21.0$ Hz, $J_{AC}=9.4$ Hz, Ar-F$^3$ (C))

$C_7H_3F_3O_3$ (192.094) % by weight calculated C 43.77 H 1.57 F 29.67 % by weight found C 43.8 H 1.6 F 29.6

IR (KBr) [cm$^{-1}$]: 3660, 3340, 3600-2200 (br), 1690, 1630, 1530, 1490, 1410, 1330, 1300, 1250, 1200, 1100, 1010, 905, 785, 740, 715, 480, 460

MS (m/z) [%]: 45 (5.2), 69 (9.5), 75 (6.1), 80 (5.9), 99 (18.3), 119 (26.5), 146 (3.8), 147 (14.1), 175 (100), 176 (9.0), 192 (69.9, M+), 193 (6.1)

The reaction scheme below serves only to illustrate the preparation of liquid-crystalline compounds using 4-hydroxy-2,3,5-trifluorobenzoic acid.

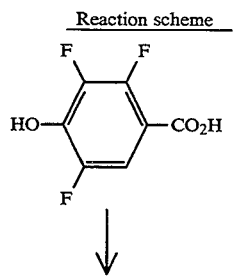

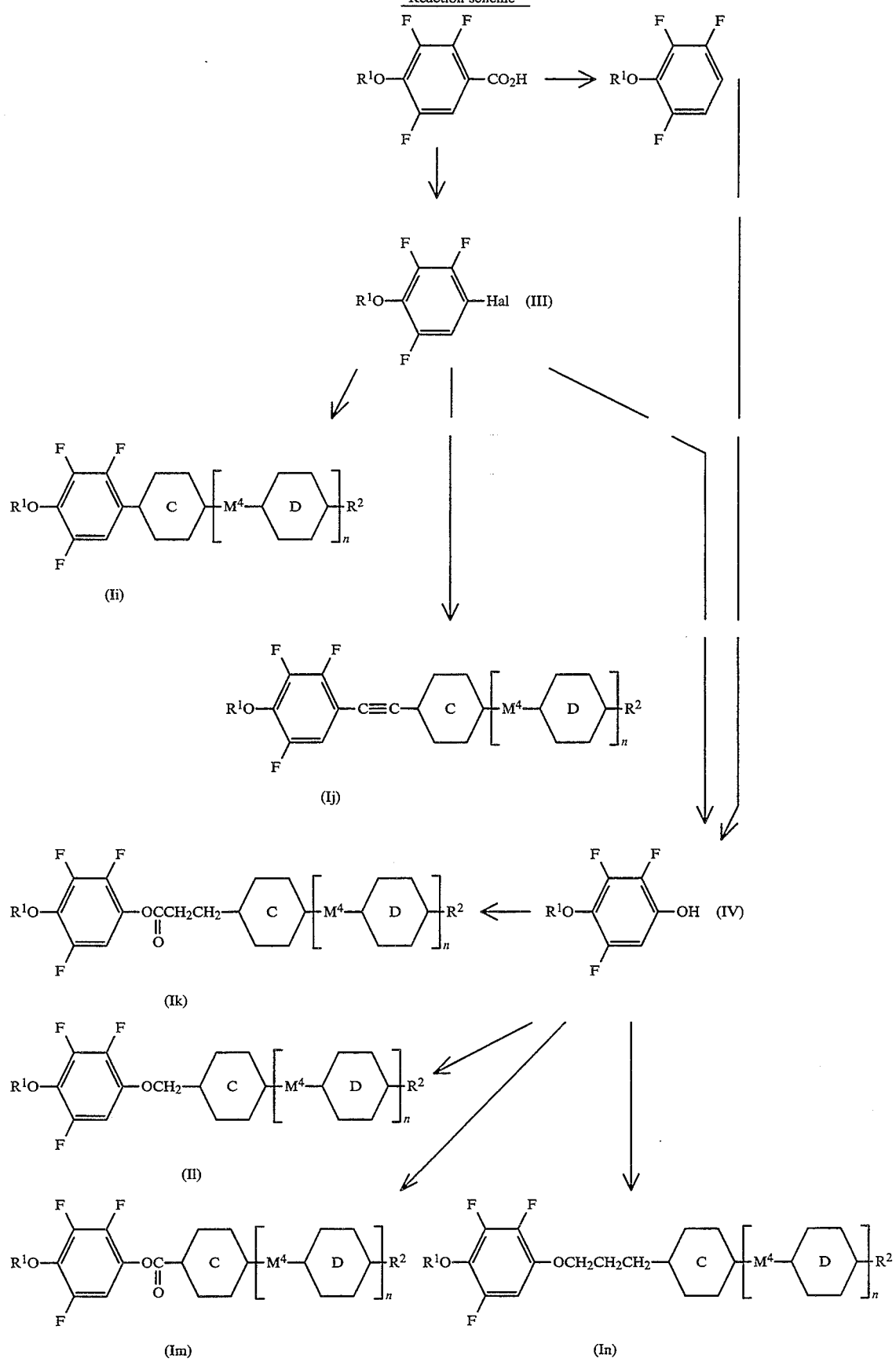

What is claimed is:
1. 4-Hydroxy-2,3,5-trifluorobenzoic acid, which has the formula
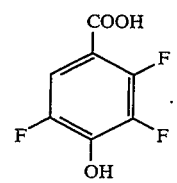

Reaction scheme